(12) United States Patent
Hartmann et al.

(10) Patent No.: US 8,309,321 B2
(45) Date of Patent: Nov. 13, 2012

(54) SCREENING METHOD FOR IDENTIFYING PROTEASE SECRETION-DEFICIENT MUTANTS OF MICROORGANISMS

(75) Inventors: Marcus Hartmann, Muenster (DE); Andre Broermann, Muenster (DE)

(73) Assignee: Cilian AG, Muenster (DE)

( * ) Notice: Subject to any disclaimer, the term of this patent is extended or adjusted under 35 U.S.C. 154(b) by 0 days.

(21) Appl. No.: 13/027,591

(22) Filed: Feb. 15, 2011

(65) Prior Publication Data

US 2011/0195443 A1    Aug. 11, 2011

Related U.S. Application Data

(63) Continuation of application No. 11/884,486, filed as application No. PCT/EP2006/060034 on Feb. 16, 2006, now abandoned.

(30) Foreign Application Priority Data

Feb. 16, 2005    (EP) .................................. 05003272

(51) Int. Cl.
    *C12Q 1/37*    (2006.01)
(52) U.S. Cl. ....................................... 435/23
(58) Field of Classification Search ............... 435/23, 435/222
    See application file for complete search history.

(56) References Cited

U.S. PATENT DOCUMENTS

| | | | |
|---|---|---|---|
| 6,153,424 A | 11/2000 | Raymond et al. | |
| 6,566,122 B1 | 5/2003 | Wange et al. | |
| 2003/0108908 A1 | 6/2003 | Rhee et al. | |

FOREIGN PATENT DOCUMENTS

WO    WO 99/14347    3/1999

OTHER PUBLICATIONS

Crandall M. et al. Segregation of Proteinase Negative Mutants from Heterozygous C. Albicans. J of General Microbiology 133:2817-2824, 1987.*
Cole E. et al. Uniparental Cytogamy . . . Genetics 132:1017-1031, Dec. 1992.*
Hunseler et al. Isolation and Characterization of a Mutant of *T. thermophilia* Blocked in Secretion of Lysosomal Enzymes. J of Cell Science vol. 88, Part 1, 47-55, Aug. 1987.*
Crandall et al. "Segragation of Proteinase Negative Mutants from Heterozygous *C. Albicans*." J og General Microbiology 133:2817-2824, 1987.
Cole et al. "Uniparental Cytogamy . . . " Genetics 132:1017-1031, Dec. 1992.
Hartmann et al. "Screening for and characterization of phopholipase A, hypersecretory mutants of *Tetrahymena thermophilia*," Applied Microbiology and Biotechnology, Springer Verlag, Berlin, DE Bd. 54: 390-396, Nr. 3, Sep. 2000.
Paech et al. "Zymogram of proteases made with developed film from nondenaturing polyacrylamide gels after electrphoresis," Analytical Biochemistry, Bd. 208: 249-254, Nr. 2, 1993.
Hunseler et al. "Isolation and characterization of a mutant of *Tetrahymena thermophilia* blocked in secretion of lysosomal enzymes." Journal of Cell Science, Aug. 1987, Bd. 88:(Pt. 1) 47-55.
Jones. "Tackling the protease problem in *Saccharmyces cerevisiae*," Methods in Enzymology, Academic Press Inc., San Diego, CA, US Bd. 194: 428-453, 1991.
Hartmann, M. et al., "Screening for and characterization of phospholipase $A_1$ hypersecretory mutants of *Tetrahymena thermophila*," Applied Microbiology and Biotechnology, Springer Verlag, Berlin, DE, Bd. 54: 390-396, Nr. 3, Sep. 2000.
Paech, C. et al.,"Zymogram of proteases made with developed film from nondenaturing polyacrylamide gels after electrophoresis," Analytical Biochemistry, Bd. 208: 249-254, Nr. 2, 1993.
Brunk, C. F., "Ciliates display promise for foreign gene expression," Nature Biotechnology, Nature Pub., US, Bd. 17: 424-425, Nr. 5, May 1999.
Hünseler P., et al., "Isolation and characterization of a mutant of *Tetrahymena thermophila* blocked in secretion of lysosomal enzymes," Journal of Cell Science, Aug. 1987, Bd. 88:(Pt. 1) 47-55.
Jones, E. W., "Tackling the Protease Problem in *Saccharomyces cerevisiae*," Methods in Enzymology, Academic Press Inc., San Diego, CA, US Bd. 194: 428-453, 1991.

* cited by examiner

*Primary Examiner* — Ralph Gitomer
(74) *Attorney, Agent, or Firm* — Jacobson Holman PLLC

(57) ABSTRACT

A method for identifying a protease secretion deficient strain of a microorganism involves producing a mutant of the microorganism, followed by adding the mutant to gel-filled wells of a microtitration plate, incubating the mutant in the gel-filled wells under conditions call sing the mutant to secrete proteins, separating the mutant from the gel, and measuring activity of a secretion protease of the microorganism in the gel, wherein either (i) the gel is a substrate for the secretion protease or (ii) the gel contains a substrate for the secretion protease.

15 Claims, 4 Drawing Sheets

SCREENING METHOD FOR IDENTIFYING PROTEASE SECRETION-DEFICIENT MUTANTS OF MICROORGANISMS

This is a continuation of Ser. No. 11/884,486, filed, May 5, 2008, abandoned, which is a 371 of PCT/EP06/060034, filed Feb. 16, 2006.

The invention relates to a method for identifying protease secretion deficient strains of microorganisms.

In biotechnology, there is a large need for expression systems with which proteins can be produced in large amounts and in the form as they occur physiologically. One of many possibilities is the heterologous expression in microorganisms which produce the proteins, optionally modify them posttranslationally and then secrete them. The basis thereof is to modify the microorganism genetically in such a way that the foreign protein is produced. The organisms in which a heterologous expression and subsequent secretion is performed include ciliates, such as *Tetrahymena*, and yeasts, such as *Pichia pastoris*.

The use of such heterologous expression systems offers many advantages. For example, it is possible to grow *T. thermophila* at low cost and within a short time to high cell densities (SALIBA et al., 1983; KIY & TIEDTKE, 1992). Further, methods have been established for genetically engineering the organism whereby foreign proteins can be produced in large amounts (TONDRAVI & YAO, 1986; YU et al., 1990; GAERTIG & GOROVSKY, 1992; GAERTIG et al., 1994; CASSIDY-HANLEY et al.; 1997). These proteins are glycosylated in a similar form as with human proteins, which renders them interesting for pharmaceutical use (TANIGUCHI et al.; 1985). One of the essential advantages of this expression system is that proteins synthesized by *T. thermophila* are secreted into the medium, which facilitates the purification of the proteins (KIY, 1993).

However, a frequent problem in the use of such heterologous expression systems is the natural secretion of proteases. Thus, for example, it is known that *T. thermophila* naturally secretes large amounts of proteases into the medium (BANNO & NOZAWA, 1982; Banno et al., 1982; Banno et al., 1983). Since these proteases have not been characterized, there is hardly any further information available. As compared to endogenous proteins, heterologously expressed proteins are significantly more susceptible to proteolytic degradation. In contrast, the functional activity of the extracellular enzymes of *T. thermophila* is essentially not limited by the secreted proteases (KIY, 1993b). A consequence of the proteolytic activity is a significant reduction of the yield of the heterologously expressed protein.

For preventing the degradation, different approaches are possible, such as the addition of protease inhibitors or of competing substrates, such as casein, or the production of strains having a lower proteolytic activity. However, there are currently no strains deficient in protease secretion available for *Tetrahymena thermophila*, for example. A mutant which is generally limited in secretion has been described (HÜNSELER et al.; 1987). However, such a mutant is not suitable for the heterologous expression of proteins, because while no proteases are secreted, the desired target proteins are not secreted either.

According to HÜNSELER et al., 1992, the secretion deficient mutant was established by a screening method. Thus, wells were punched into an agar plate and sucked off with a pipette. Then, cell cultures are added to these wells. The method is relatively tedious and cannot be automated. There is also a risk of cross contaminations when the thin agar layer is damaged. Also, the method cannot be used at a large scale or automated.

Generally, for secreting expression systems, there is a large need for strains having a low proteolytic activity or none at all.

A method for the screening for hypersecretory mutants of *T. thermophila* has been developed (HARTMANN, 2000). In this method, the mutants are grown in 96-well microtitration plates. The cells are then separated off by ultracentrifugation into a zone of different density. A layer of a polymer (Ficoll) is placed below each of the cultures, and the cells are centrifuged into the Ficoll. The supernatant was removed with a pipette. In enzyme tests, mutants were determined which had an increased activity of secreted proteins, such as β-hexaminidase and acid phosphatase.

This method requires a high expenditure of time. Further, it cannot be excluded that cell lysis occurs in which non-secreted proteins are released which change the result.

It is the object of the invention to provide a method for the screening for improved secretion systems for the heterologous expression of proteins. In particular, the method shall enable the screening for mutants of microorganisms which have an improved yield of secreted heterologously expressed proteins.

The method shall enable a large number of mutants to be tested in a short time and at moderate cost.

Surprisingly, the object of the invention is achieved by a method and microorganisms produced thereby, i.e., (1) a method for identifying protease secretion deficient strains of a microorganism, wherein: mutants of the microorganism are produced: a gel is produced in the wells of a microtitration plate a microorganism added is added to each of the wells onto the gel; incubation is effected under conditions under which the mutants of the microorganism secrete proteins; the mutants of the microorganism are separated from the gel; wherein at least one substrate for at least one secretion protease of the microorganism is contained in the gel and/or the gel itself is the substrate and/or the substrate is added later and will at least in part diffuse into the gel; and the protease activity that has acted on the substrate is measured: 2 the method (1) wherein the microorganism is selected from the group consisting of ciliates, especially *Tetrahymena*, yeasts, especially *Pichia pastoris*, monocellular algae, especially *Chlamydomoxnas*, *Ulva* and *Euglena*, and prokaryotes, especially *Bacillus* and *Escherichia*; (3) the method (1) or (2) wherein the mutants of the microorganism are produced by random mutagenesis or directed mutagenesis; (4) the method (1) or (2) wherein the mutants of the microorganism are produced by uniparental cytogamy (UPC); (5) any method (1) to (4) wherein the incubation of the mutants of the microorganism with the gel is effected in a nutrient medium; (6; (5) wherein the nutrient medium contains skim milk powder, proteose peptones, yeast extract, soybean peptones, ferrous sulfate/chelate solution and/or glucose monohydrate or is a synthetic medium; (7) any method (1) to (6) wherein the gel is a gelatin, agarose, agar and/or polyacrylamide gel; (8) any method (1) to (7) wherein the substrate for the protease is selected from the group consisting of casein, derivatives of casein, fluorescence-labeled casein and/or gelatin; (9) any method (1) to (8) wherein the incubation is effected under conditions under which the microorganism secretes proteases, and secreted proteases can diffuse into the gel; (10) any method (1) to (9) wherein the microorganism is separated from the gel by pouring (decanting), pipetting, sucking and/or washing; (11) any method (1) to (10) wherein the proteolysis of the substrate produces a fluorescence signal or absorption signal whose intensity is measured, and the protease activity is determined from the results; (12) any method (1) to (11) wherein a layer of the gel is applied to a film, changes of the film are measured, and the protease activity is determined from these changes; (13; (12) wherein the film is an X-ray film; (14) any method (1) to (13) wherein the method is performed in an automated format; and (15) the protease secretion deficient microorganisms obtainable by any method (1) to (14).

Figure 1:
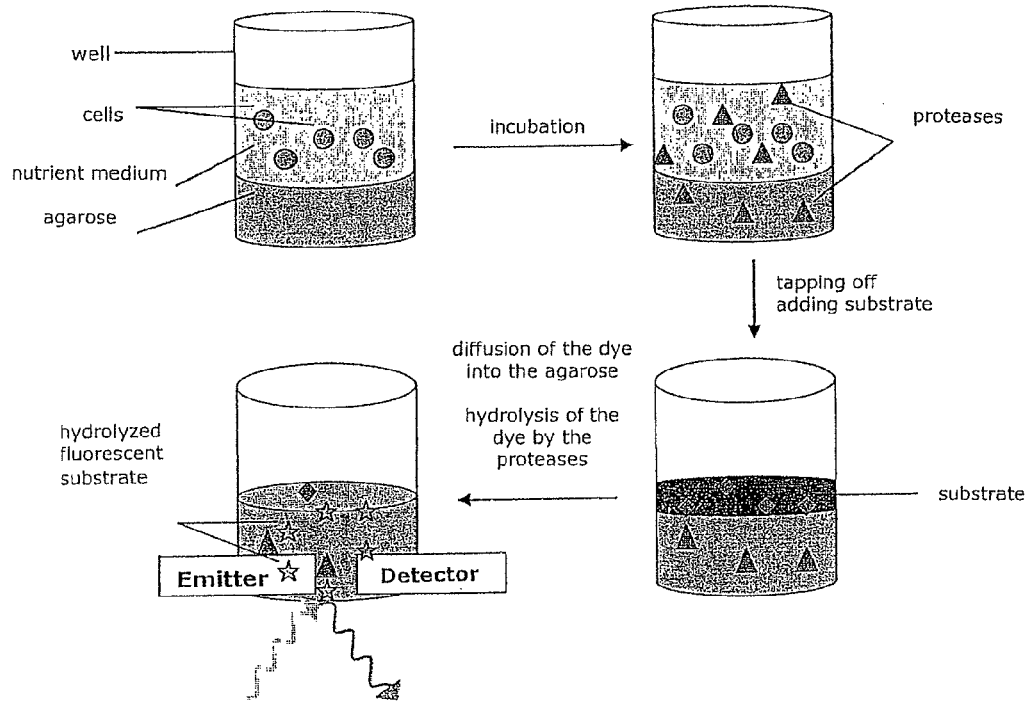
FIG. 1 shows a schematic set-up of a fluorescence screening method according to the invention.

Generally, the method can be performed with mutants of microorganisms which secrete proteases and are suitable for the secretion of heterologously expressed target proteins. The term "secretion proteases" means those proteases secreted by the wild type of the microorganism into its environment. The method according to the invention enables the measurement of protease activity in vivo.

The microorganism is preferably selected from the group consisting of ciliates and yeasts. Such microorganisms express endogenous proteins having enzymatic activity, such as proteases. Particularly suitable yeasts include *Pichia pastoris*. The method is also suitable for the screening for monocellular algae, especially *Chlamydomonas, Ulva* and *Euglena*, and prokaryotes, especially *Bacillus* and *Escherichia*. Particularly suitable ciliates are those of the genus *Tetrahymena*, especially *Tetrahymena thermophila, malaccensis, elliotti, alphaeliotti, pyriformis, setosa, alphapyriformis, betapyriformis, leucophrys, silvani, vorax, tropicalis, alphatropicalis, betatropicalis, gammatropicalis, delta tropicalis, borealis, canadensis, rostrata, alphacanadensis, betacanadensis, mimbres, americanis americanis, paraamericanis, australis, hegewischi, hyperangularis, nanneyi, nippisingi, pigmentosa, pigmentosa oriasi, pigmentosa europigmentosa, sonneborni, asiatica, capricomis, patula, allensae, cosmopolitanis or shanghaiensis*.

The mutants of the microorganisms can be produced by known methods, such as random mutagenesis or directed mutagenesis. The method is particularly advantageous for microorganisms in which protease secretion deficient strains are not available, or only with difficulty, for technical reasons or due to a lack of genetic information. Cross-genetic methods are particularly preferred.

A particularly preferred method for producing the mutants is uniparental cytogamy. This is a cross-genetic method. It is preferably performed as described by Cole and Bruns (1992). The method described therein is incorporated herein by reference. This method allows up to 20 times as many mutations to become expressive as, for example, the short-circuit genome exclusion method used by Hünseler et al. (1987). Thus, the mutation yield is higher by a factor of 20.

The incubation of the mutant of the microorganism with the gel is preferably effected in a suitable aqueous medium, preferably a nutrient medium. At any rate, conditions (pH value, ion concentration etc.) similar to physiological conditions should prevail, so that dying and lysing of the microorganisms is prevented.

In preferred embodiments, the incubation of the microorganisms with the gel is performed for 2 hours to 2 weeks, especially 1 to 5 days.

Suitable nutrient media are or contain skim milk powder, proteose peptones, yeast extract, soybean peptones, ferrous sulfate/chelate solution (100X, Sigma) and/or glucose monohydrate. A chemically defined medium (CDM) according to an exact formulation of the individual ingredients may also be used.

In preferred embodiments, a gelatin, agarose, agar and/or polyacrylamide gel is used as the gel. The pore size or degree of cross-linking is selected in such a way that secreted proteins, such as proteases, can diffuse into the gel while the microorganisms are essentially excluded from the gel.

In preferred embodiments, the substrate for the protease is selected from the group consisting of casein, derivatives of casein, fluorescence-labeled casein and/or gelatin. Particularly suitable are BODIPY FL Casein and BODIPY TR-X Casein (Molecular Probes Inc., USA) or similarly fluorescence-labeled peptides or proteins.

The incubation is preferably effected under conditions under which the microorganism secretes proteases, and secreted proteases can diffuse into the gel.

The separating of the microorganism from the gel is preferably effected by pouring (decanting), pipetting, sucking and/or washing.

In a preferred embodiment, the proteolysis of the substrate produces a fluorescence or absorption signal whose intensity is measured, and the protease activity is determined from the result.

In a further preferred embodiment, a layer of the gel is applied to a film, especially an X-ray film. After the protease has acted on the substrate, changes of the film are measured, and the protease activity is determined from these changes.

The method according to the invention is performed by using a microtitration plate. A gel is produced in each of the wells of the plate. This is usually done by pouring a solution, for example, an agarose solution, into the wells followed by cooling. Usual microtitration plates with 96 wells are preferred. The method of the invention can be automated and/or performed by using a large number of mutants to be tested. One mutant is added to each well of the microtitration plate. This need not mean that only a single cell is added. A large number of cells having identical DNAs may also be added. Such a large number of cells is produced by isolating a cell and then propagating it.

The method of the invention enables the selective screening for mutants which specifically secrete no or less active proteases into the medium, while the secretion of other proteins and at least of the heterologously expressed proteins is preferably not limited or only slightly so. For the functioning of the assay, it is irrelevant whether the proteases are secreted in an inactive form or not at all. The critical point is that the reduced protease activity results in an increase of the yield of the target protein.

Methods for generating mutants of ciliates by random mutagenesis have been established (CRUEGER & CRUEGER, 1989). Also, cross-genetic maneuvers have been described by means of which a mutation can be brought to expression (COLE & BRUNS, 1989). These methods are necessary due to the nuclear dimorphism in *T. thermophila*. Further, it is possible to distribute the mutants to 96-well microtitration plates using a distributor apparatus and Poisson lottery.

The method according to the invention has numerous advantages over known methods:

The method is specific because mutants whose secretion system is generally adversely affected and which therefore would not be suitable for the heterologous secretion of other proteins are not established.

A signal is produced exclusively by the activity of the secreted proteases in the medium. Due to the mild assay conditions, no cell lysis occurs during the screening, and thus the result is not biased by intracellular proteases.

Various non-specific protease substrates can be employed. This is advantageous because little is known about the substrate specificity of secreted proteases, for example, in ciliates. Thus, the screening yields results which affect the whole protease activity.

The method according to the invention can be performed simply and quickly and allows the examination of ciliate cultures in their nutrient medium. Thus, purification steps such as the centrifugation in the method according to Hartmann et al. (2000) are omitted. The simple method allows large amounts of mutants to be tested for the activity of extracellular proteases, for example, on a 96-well scale.

Especially when a large number of mutants is produced by uniparental cytogamy (UPC), a very high efficiency is achieved.

The method yields mutants which can subsequently be analyzed more closely with respect to their secretion properties. The strains obtained can then be utilized as heterologous expression systems.

The method makes use of the diffusion of expressed proteases into a gel. Methods for finding proteases in which the proteases are transferred to a gel had been known already according to the prior art, for example, Paech et al., 1993. These are methods in which the proteases are purified before entering the gel on the one hand, and separated by electrophoresis in the gel on the other. The method according to the invention is completely different since purification of the proteases is not required and since no electrophoresis or application of electric voltage takes place.

A screening method according to the invention can be performed as follows, for example:

The mutants are grown in the wells of a 96-well microtitration plate. The cultures are in a liquid nutrient medium which is below a layer of agarose. During incubation, the extracellular enzymes, including the proteases, in part diffuse into the agarose. After the nutrient medium with the cells has been tapped off, a casein derivative is added to the agarose, which also in part diffuses into the agarose. If this casein derivative is cleaved by proteolytic activity, a fluorescence signal is generated which is proportional to the protease activity. The intensity of the signal can be detected, for example, by means of a microtitration plate fluorescence reader within the scope of an end-point determination or by recording the kinetics. A low fluorescence signal is an indication of a protease secretion deficient strain.

In a further embodiment, a screening method according to the invention can be performed as follows:

The cultures which had already been cultured for some time in microtitration plates are applied in spots to the gelatin-coated side of a fully exposed and developed X-ray film by means of an eight-channel pipette. The drops consist of nutrient medium into which the extracellular enzymes had been secreted already during the incubation. Further, the cells are present in the medium. In order to prevent cell lysis, care is to be taken that the drops do not dry out. The drops remain on the gelatin for some time, so that the latter can be hydrolyzed by the proteases present. When the drops are then washed off the film and the film is subsequently placed into a special buffer, clearing halos are formed at the places where gelatin was hydrolyzed. Thus, such a clearing halo is an indication of high activity of extracellular proteases.

The methods according to the invention are characterized in that the activity of the proteases is selectively detected in the supernatant without complicated methods for obtaining a cell-free supernatant being necessary. Further, it is possible to test the strains for activity of proteases that are not further characterized, because non-specific substrates (casein derivatives, gelatin) are employed. Both methods are characterized by being quickly performed and by low cost, so that a large number of mutants can be tested.

EXAMPLES

Method 1

The mutations are produced by chemical random mutagenesis and subsequently brought to expression by the cross-genetic method of uniparental cytogamy (briefly: UPC) according to COLE and BRUNS, 1992. Thus, mutants were generated. After the mutants had been prepared, microtitration plates for the screening were prepared as follows:

Into the wells of a 96-well microtitration plate, agarose (1%; w/v) is poured under sterile conditions. After having solidified, the agarose is covered by a layer of nutrient medium. The inoculation of the wells with the mutagenized strains of *Tetrahymena* is effected by means of a self-prepared 96 stamp starting from the previously prepared microtitration plates in which the clones were grown. After three days of incubation at 30° C., the nutrient medium with the cells is tapped out (decanted), and the wells are washed twice with buffer (Tris-HCl; 50 mM; pH 7.4). Into the wells, 100 μl each of fluorescence dye is placed as a substrate for the enzyme reaction. As substrates, those contained in the EnzChek Protease Assay Kit E-6638 (Molecular Probes Inc. USA) are employed. The dye is used in accordance with the manufacturer's instructions, wherein the solution to be used is diluted 1:2 with the supplied buffer. Due to the dilution, the number of samples can be increased significantly without affecting the sensitivity of the test (FIG. 1).

For the detection of the fluorescence intensity, the Reader FLx800 (BIO-TEK INSTRUMENTS, INC.) with a pair of filters adapted to the excitation and detection wavelengths is used. As a measure of protease activity, kinetics can be recorded directly after the addition of the substrate, wherein the slope is proportional to the fluorescence signal and thus also to the protease activity.

Alternatively, it is possible to perform an end-point measurement after one hour of incubation at room temperature. The absolute values thus obtained also reflect the fluorescence intensity or the protease activity.

Method 2

The mutations are produced by chemical random mutagenesis and subsequently brought to expression by the cross-genetic method of uniparental cytogamy (briefly: UPC) according to COLE and BRUNS, 1992. Thus, mutants were generated. After the mutants had been prepared, microtitration plates for the screening were prepared as follows:

Gelatin-coated X-ray films (Ferrania) are exposed, developed and fixed. Prior to use, the films are wetted with buffer (Tris-HCl; 50 mM; pH 7.5) for 10 min. After this pretreatment, the residues of the buffer must be carefully removed with filter paper. To the gelatin-coated side, 30 μl of three days old cultures of *Tetrahymena* are applied by means of an eight-channel pipette. It is to be taken care that the drops do not bleed into one another. While the films with the drops are incubated at 30° C. for one hour, the proteases present in the medium hydrolyze the gelatin, wherein the cells within the drop survive. After the lapse of the incubation time, the drops are rinsed off the films with distilled water. Upon another minute of incubation of the film in glycine buffer (0.1 M; pH 10.0; 50° C.), clearing halos can be observed in the places where the gelatin was degraded. Without the gelatin layer, the silver compound that causes the black staining is washed out. Thus, whether or not washing out occurs depends on the level of activity of the secreted proteases. Also, the degradation of the gelatin is influenced by the parameters incubation time and incubation temperature, so that the test must be adapted to the respectively prevailing conditions.

By means of these novel screening methods, a mutant of *Tetrahymena* could be isolated which secretes clearly less active proteases into the nutrient medium while the secretion of other enzymes, such as β-hexaminidase and acid phosphatase, is essentially not reduced.

Thus, by means of the novel screening method, mutants can be prepared that are secretion deficient exclusively for proteases, but are not generally limited in their ability to release proteins into the surrounding culture medium. This becomes clear when the secretion kinetics of a typical mutant obtained with the novel screening method are compared to the secretion kinetics of wild type strains.

Figure 3:
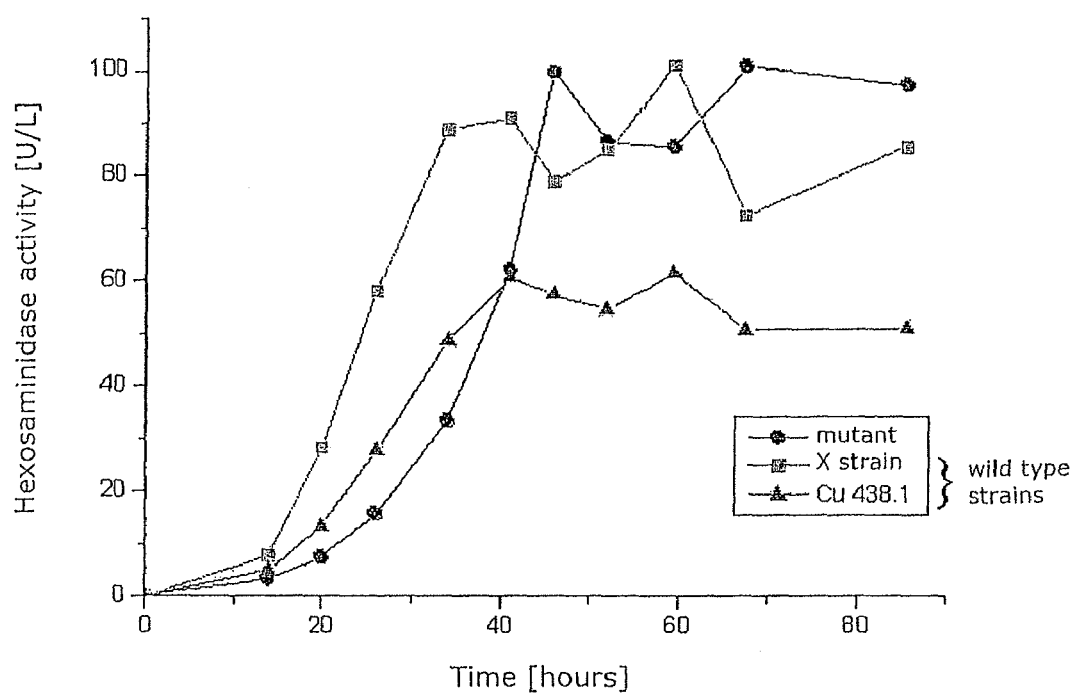
FIG. 3 shows secretion kinetics with volume activities of β-hexosaminidase in a cell-free supernatant of a mutant and the two wild type strains X and Cu 438.1.
Figure 4:
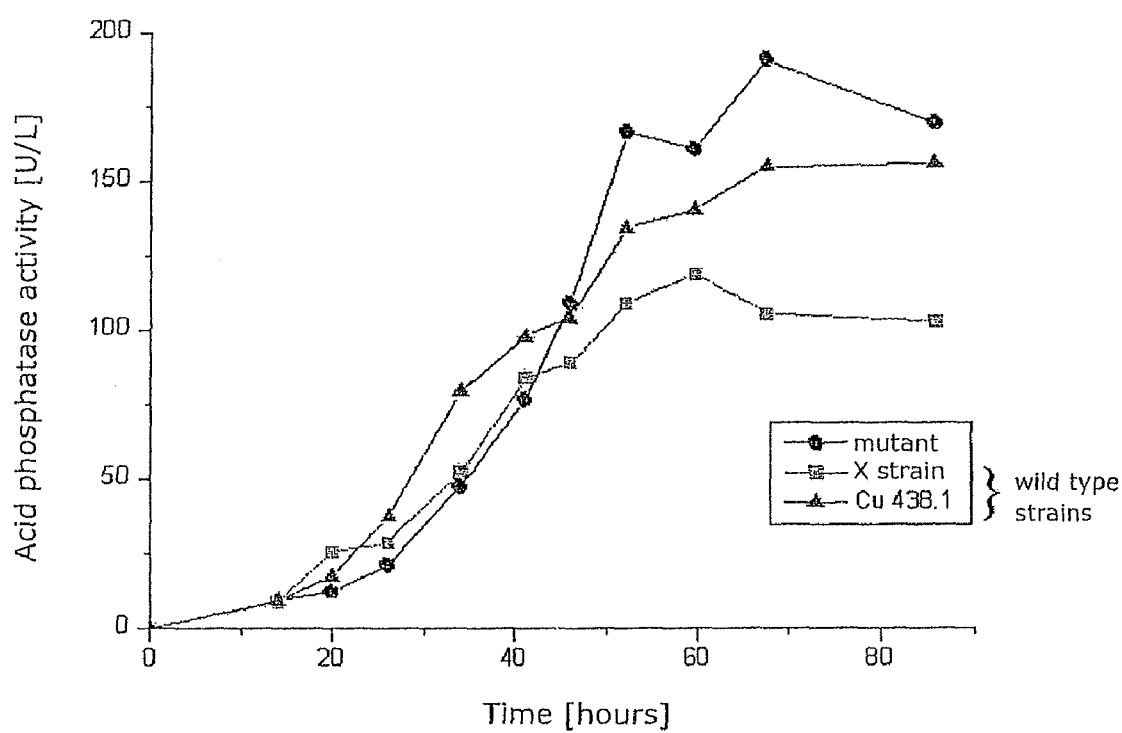
FIG. 4 shows secretion kinetics with volume activities of acid phosphatase in a cell-free supernatant of a mutant and the two wild type strains X and Cu 438.1.
Figure 5:
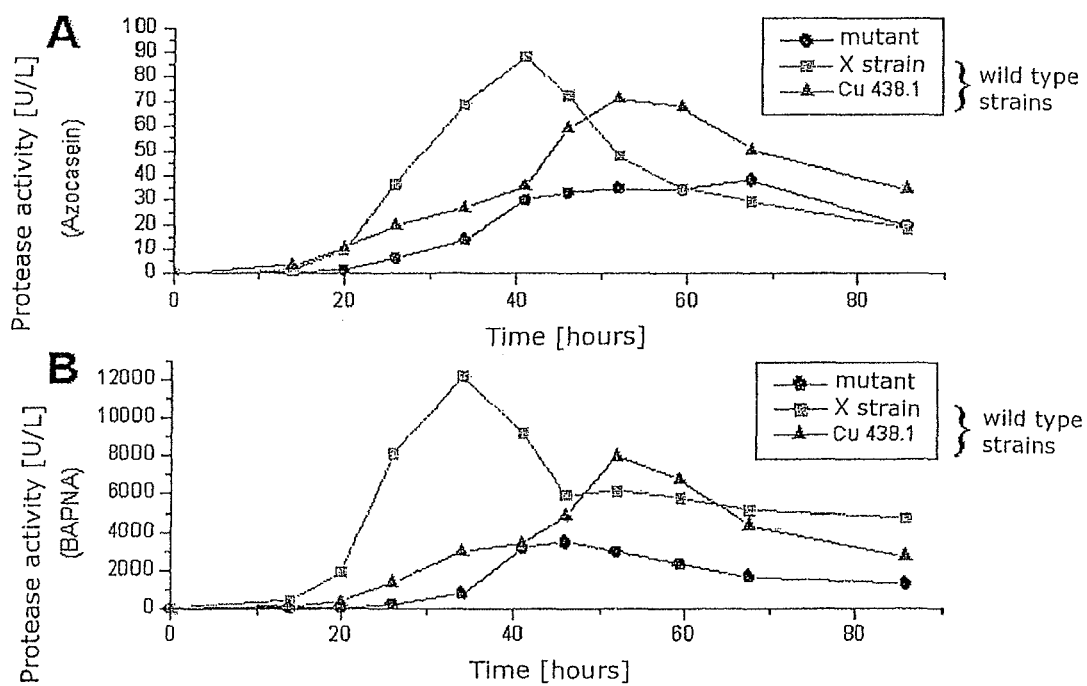
FIG. 5 shows secretion kinetics with volume activities of the proteases in a cell-free supernatant of a mutant and the two wild type strains X and Cu 438.1.

FIGS. 3 and 4 show secretion kinetics of a mutant in comparison to wild type strains (wild type strain X and wild type strain CU 438.1). The volume activities for two typical secreted lysosomal enzymes, beta-hexosaminidase and acid phosphatase, for the mutant are comparable to the volume activities for wild types. FIG. 5 shows secretion kinetics for protease of one mutant and two wild types. It becomes clear that the mutant releases clearly less protease into the surrounding culture medium during the duration of the culture as compared to the wild type strains.

FIGURES

FIG. 1 shows a schematic set-up of a fluorescence screening method according to the invention.

Figure 2:
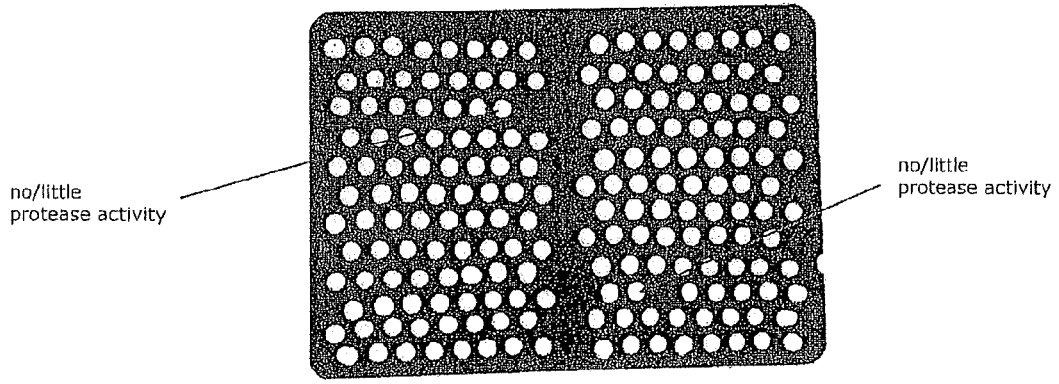
FIG. 2 shows an X-ray film after the screening has been performed.

FIG. 2 shows an X-ray film after the screening has been performed.

FIG. 3 shows secretion kinetics with volume activities of β-hexosaminidase in a cell-free supernatant of a mutant and the two wild type strains X and Cu 438.1.

FIG. 4 shows secretion kinetics with volume activities of acid phosphatase in a cell-free supernatant of a mutant and the two wild type strains X and Cu 438.1.

FIG. 5 shows secretion kinetics with volume activities of the proteases in a cell-free supernatant of a mutant and the two wild type strains X and Cu 438.1.

REFERENCES

BANNO, Y. & NOZAWA, Y. (1982): Changes in particulate-bound protease activity during cold acclimation in *Tetrahymena pyriformis*; Biochim. Biophys. Acta 719: 20-28

BANNO, Y., YANO, K. & NOZAWA, Y. (1982): Biochemical characterization of secreted proteases during growth in *Tetrahymena pyriformis* WH-15: Comparison of extracellular with intracellular proteases; J. Protozool. 29: 91-98

BANNO, Y., YANO, K. & NOZAWA, Y. (1983): Purification and characterization of a secreted protease from *Tetrahymena pyriformis*; Eur. J. Biochem.

CASSIDY-HANLEY, D., BOWEN, J., LEE, J. H., COLE, E., VERPLANKT, L: A., GAERTIG, J., GOROWSKY, M. A. & BRUNS, P. J. (1997): Germline and somatic transformation of mating *Tetrahymena thermophila* by particle bombardment; Genetics 146: 135-147

COLE, E. S. & BRUNS, P. J. (1992): Uniparental Cytogamy: A novel method for bringing micronuclear mutations of *Tetrahymena* into homozygous macronuclear expression with precocious sexual maturty; Genetics 132: 1017-1031

CRUEGER, W. & CRUEGER, A. (1989): Biotechnologie—Lehrbuch der angewandten Mikrobiologie-3. Aufl.: 3. Stammentwicklung: 7-54; Oldenburg Verlag GmbH, München GAERTIG, J., & GOROVSKY, M. A. (1992): Efficient mass transformation of *Tetrahymena thermophila* by electroporation of conjugants; Proc. Natl. Acad. Sci. USA 89: 9196-9200

GAERTIG, J., GU, L., HAI, B. & GOROVSKY, M. A. (1994): High frequent vector-mediated transformation and gene replacement in *Tetrahymena*; Nucleic Acids Res. 22: 5391-5398

HARTMANN, M., GUBERMANN, A., FLORIN-CHRISTENSEN, M. & TIEDTKE, A. (2000): Screening for and characterization of phospholipase $A_1$ hypersecretory mutants of *Tetrahymena thermophila*; Appl. Microbiol. Biotechnol. 54: 390-396

HÜNSELER, P., SCHEIDGEN-KLEYBOLDT, G. & TIEDTKE, A. (1987): Isolation and characterization of a mutant of *Tetrahymena thermophila* blocked in secretion of lysosomal enzymes; J. Cell Sci. 88: 47-55

KIY, T. & TIEDTKE, A. (1992): Continous high-cell-density fermentation of the ciliated protozoon *Tetrahymena* in a perfused bioreactor; Appl. Microbiol. Biotechnol. 38: 141-146

KIY, T. (1993): Fermentation von Ciliaten zur Produktion biogene Wertstoffe; Inaugural-Dissertation zur Erlangung des Doktorgrades; Institut für Allgemeine Zoologie and Genetik, Westfälische Wilhelms-Universität Münster PAECH, C., CHRISTIANSON, T., & MAURER, K.-H. (1993): Zymogram of proteases made with developed film from non-denaturing polyacrylamide gels after electrophoresis; Analyt. Biochem. 208: 249-254

TANIGUCHI, T., MIZUOCHI, T., BANNO, Y., NOZAWA, Y. & KOBATA, A. (1995): Carbohydrates of lysosomal enzymes secreted by *Tetrahymena pyriformis*; J. Biol. Chem. 260 (26): 13941-13946

TONDRAVI, M. M., & YAO, M.-C. (1986): Transformation of *Tetrahymena thermophila* by microinjection of ribosomal RNA genes; Proc. Natl. Acad. Sci. USA83: 4369-4373

YU, G. L., BRADLEY, ATTARDI, L. D. & BLACKBURN, E. H. (1990): In vitro alteration of telomere sequences and senescence caused by mutated *Tetrahymena* telomerase RNAs; Nature 344: 126-132

The invention claimed is:

1. A method for identifying a protease secretion deficient strain of a microorganism not deficient in desired protein target secretion comprising the steps of
producing a mutant of a wild type microorganism, followed by
adding the mutant to gel-filled wells of a microtitration plate,
incubating the mutant in the gel-filled wells under conditions causing the mutant to secrete proteins,
separating the mutant from the gel, and
measuring activity of a secretion protease of the microorganism in the gel, wherein either (i) the gel is a substrate for the secretion protease or (ii) the gel contains a substrate for the secretion protease, a measurement of reduced protease activity compared to the wild type identifying the mutant as a protein deficient strain, and measuring desired protein target secretion in the gel and comparing the measured secretion with desired protein target secretion of the wild type, to confirm whether the mutant is not deficient in desired protein target secretion.

2. The method of claim 1 wherein the microorganism is selected from the group consisting of ciliates, yeasts, monocellular algae, and prokaryotes.

3. The method of claim 1 wherein the microorganism is selected from the group consisting of *Tetrahymena, Pichia pastoris, Chlamydomonas, Ulva, Euglena, Bacillus*, and *Escherichia*.

4. The method according to claim 1 wherein the mutant is produced by random mutagenesis or directed mutagenesis.

5. The method according to claim 1 wherein the mutant is produced by uniparental cytogamy (UPC).

6. The method according to claim 1 wherein the gel is a nutrient medium.

7. The method according to claim 6 wherein the nutrient medium comprises at least one of skim milk powder, proteose peptones, yeast extract, soybean peptones, ferrous sulfate/chelate solution, and glucose monohydrate or the nutrient medium is a synthetic medium.

8. The method according to claim 1 wherein the gel comprises gelatin, agarose, agar, polyacrylamide or a combination of two or more thereof.

9. The method according to claim 1 wherein the substrate for the protease is at least one of casein, a derivative of casein, fluorescence-labeled casein, and gelatin.

10. The method according to claim 1 wherein the incubation is effected under conditions whereby secreted proteases diffuse into the gel.

11. The method according to claim 1 wherein the microorganism is separated from the gel by at least one of pouring (decanting), pipetting, sucking, and washing.

12. The method according to claim 1 wherein secreted proteases effect proteolysis of the substrate to produce a fluorescence signal or absorption signal, and measuring activity of a secretion protease is determined by measuring intensity of the signal.

13. The method according to claim 1 wherein the substrate is a film and measuring the protease activity is determined by changes in the film.

14. The method according to claim 13 wherein the film is an X-ray film.

15. The method according to claim 1 performed in an automated format.

* * * * *